United States Patent
Cai et al.

(10) Patent No.: US 10,980,541 B2
(45) Date of Patent: Apr. 20, 2021

(54) ABSORBABLE AND UNIDIRECTIONALLY COMPRESSIBLE INTESTINE-INTESTINE STAPLER

(71) Applicant: ZHEJIANG UNIVERSITY, Zhejiang (CN)

(72) Inventors: Xiujun Cai, Hangzhou (CN); Mingyu Chen, Hangzhou (CN); Chen Lu, Hangzhou (CN); Yifan Wang, Hangzhou (CN); Diyu Huang, Hangzhou (CN); Hepan Zhu, Hangzhou (CN); Yibin Zhu, Hangzhou (CN); Bin Zhang, Hangzhou (CN)

(73) Assignee: Zhejiang University, Zhejiang (CN)

( * ) Notice: Subject to any disclaimer, the term of this patent is extended or adjusted under 35 U.S.C. 154(b) by 146 days.

(21) Appl. No.: 16/337,849

(22) PCT Filed: Jul. 17, 2017

(86) PCT No.: PCT/CN2017/093163
§ 371 (c)(1),
(2) Date: Mar. 28, 2019

(87) PCT Pub. No.: WO2018/059084
PCT Pub. Date: Apr. 5, 2018

(65) Prior Publication Data
US 2020/0029968 A1  Jan. 30, 2020

(30) Foreign Application Priority Data
Sep. 29, 2016 (CN) .......................... 201610863689.X (51) Int. Cl.
*A61B 17/11* (2006.01)
*A61B 17/00* (2006.01)

(52) U.S. Cl.
CPC . *A61B 17/1114* (2013.01); *A61B 2017/00004* (2013.01); *A61B 2017/1103* (2013.01); *A61B 2017/1132* (2013.01)

(58) Field of Classification Search
CPC .. A61B 2017/1132; A61B 2017/00004; A61B 2017/00818; A61B 2017/1142;
(Continued)

(56) References Cited

U.S. PATENT DOCUMENTS

| 4,552,148 A * | 11/1985 | Hardy, Jr. ........... A61B 17/1114 606/154 |
| 2007/0142850 A1 * | 6/2007 | Fowler .................. A61B 17/11 606/153 |

(Continued)

FOREIGN PATENT DOCUMENTS

| CN | 102112069 A | 6/2011 |
| CN | 203970452 U | 12/2014 |

(Continued)

*Primary Examiner* — Elizabeth Houston
*Assistant Examiner* — Lauren Dubose
(74) *Attorney, Agent, or Firm* — Muncy, Geissler, Olds & Lowe, P.C.

(57) ABSTRACT

An absorbable and unidirectionally compressible intestinal anastomosis device, including a first through pipe portion and a second through pipe portion respectively including large ends and small ends; the large ends are used for fixing an intestinal canal; and the small end of the second through pipe portion is inserted into the small end of the first through pipe portion. The two large ends are drawn close to each other to achieve an intestine-intestine anastomosis. The outer sides of circular rings at the ends of the small ends of the first through pipe portion and the second through pipe portion are provided with gradually-expanded elastic horn- (Continued)

shaped openings. The device can make two stapled intestinal canals rest relatively, thereby avoiding adjustments required in other assembling modes.

5 Claims, 6 Drawing Sheets

(58) Field of Classification Search
CPC .......... A61B 2017/00477; A61B 2017/00862; A61B 2017/1107; A61B 17/11; A61B 17/1155; A61B 17/1114; A61M 39/10; A61M 39/105; A61M 2039/1027; A61M 2039/1066; A61M 2039/1083; A61M 2039/1088; A61F 2/82; A61F 5/445; A61F 2007/0228
See application file for complete search history.

(56) References Cited

U.S. PATENT DOCUMENTS

| | | | | |
|---|---|---|---|---|
| 2009/0012543 | A1* | 1/2009 | Kansoul | A61B 17/11 606/153 |
| 2019/0038288 | A1* | 2/2019 | Rosello | A61B 17/11 |

FOREIGN PATENT DOCUMENTS

| | | |
|---|---|---|
| CN | 105078535 A | 11/2015 |
| CN | 105120773 A | 12/2015 |
| CN | 106308866 A | 1/2017 |
| CN | 206403818 U | 8/2017 |

\* cited by examiner

ABSORBABLE AND UNIDIRECTIONALLY COMPRESSIBLE INTESTINE-INTESTINE STAPLER

TECHNICAL FIELD

The present invention relates to an absorbable and unidirectional compressive intestinal anastomosis device.

BACKGROUND

Intestinal anastomosis is one of the most common operations in abdominal surgery, and it is also the surgical technique that surgeons must master. It is the key technology for digestive tract reconstruction and is related to the success or failure of surgery. Ideal bowel anastomosis should avoid complications such as anastomotic leakage, stenosis, hemorrhage, etc., and is easy to operate. Improvement and innovation matching technology has always been a hot topic in external scientific research. Up to now, hundreds of anastomotic methods have been developed. These methods have their own advantages and disadvantages, but none of them can fully meet the above requirements. For example, the most commonly used manual suture method and stapler method in clinical practice can not completely avoid complications such as anastomotic leakage, stenosis and hemorrhage.

At present, the traditional intestinal suture anastomosis and tubular stapler are mainly used.

Conventional manual suture anastomosis, that is, the surgeon uses a conventional surgical method to manually suture and knot with a needle holder, forceps, and needle thread.

The tube-type stapler is placed in one end of the intestine tube, and the other end of the excitation rod is placed again, and the end-end anastomosis is performed, but the tube-type stapler is mainly applied to the rectum and part of the sigmoid colon. Intestinal anastomosis requires an additional small opening and suturing the small opening.

The linear cutting and closing device improves the intestinal anastomosis. This method can correct the end-to-end anastomosis of the intestine, but it changes the original structure of the digestive tract.

In summary, the traditional intestinal anastomosis has the disadvantages of high operational difficulty and high incidence of postoperative anastomotic leakage; while the tubular stapler is suitable for a small range of intestinal tubes; in addition, the above traditional anastomosis is more difficult to be performed under laparoscopy, and the main problem of anastomotic leakage can't be effectively solved.

SUMMARY OF THE INVENTION

In order to overcome the above-mentioned defects of the existing anastomosis manner, the present invention provides an absorbable and unidirectional compressive intestinal anastomosis device for reducing the incidence of anastomotic leakage, reducing the difficulty of intestinal anastomosis, accelerating the progress of the operation, especially the difficulty of laparoscopic intestinal anastomosis, and shortening the operation time, Expandable intestinal anastomosis, especially expanding the scope of application of the absorbable and unidirectional compressive end-to-end anastomosis.

The technical solution adopted by the invention is:

an absorbable and unidirectional compressive intestinal anastomosis device, comprising a first through pipe portion 1 and a second through pipe portion 2 which are matched mutually and which are made of a human acceptable degradation material; the first through pipe portion 1 can move back and forth relative to the second pipe portion 2 along a common axial direction thereof, and the first through pipe 1 and the second through pipe 2 are inseparable; The first through pipe portion 1 and the second through pipe portion 2 respectively comprise a large end (11,21) and a small end, and the large ends (11,21) are for fixing the intestinal canal, and the small end of the second through pipe portion 2 is sheathed into the small end of the first through pipe portion 1. The two large ends (11, 21) are consistent in size; when the first through pipe portion 1 moves relative to the second through pipe portion 2, the two large ends (11, 21) are drawn close to each other to achieve an intestine-intestine and end-end anastomosis.

Each of the inner side of the large end of the first through pipe portion 1 and the inner side of the large end of the second through pipe portion 2 is provided a circle of boss (14,24), and a plurality of through grooves 22 are provided on the inner side of the wall of the large end of the second through pipe portion 2 at intervals in the circumferential direction, a plurality of first racks 12 at intervals in the circumferential direction form the wall of the small end of the first through pipe part 1 in the axial direction, the first rack 12 penetrates through the through groove 22 and is movable along the through groove 22;

A plurality of second racks 23 at intervals in the circumferential direction form the wall of the small end of the second through pipe portion 2, and there is a sliding groove 13 at every abutment of the first racks 12 and the second racks 23; the second rack 23 and the first rack 12 are arranged in a staggered mode, the first rack 12 and the second rack 23 are matched to form a closed space;

The tail ends of the first racks 12 and that of the second racks 23 are connected through a circular ring (15,25) respectively;

The outer side of circular ring at the ends of the small end of the first through pipe portion 1 and that of the second through pipe portion 2 are provided with gradually-expanded elastic horn-shaped openings 4 respectively; when the first through pipe portion 1 closes up or opens relative to the second through pipe portion 2, the elastic horn-shaped openings 4 of the two ends open or are squeezed into the large ends 11 of the first through pipe portion 1 or the large ends 21 of the second through pipe portion 2 respectively.

The invention further comprises an annular structure 3 which is arranged in the circumferential direction and is used for reinforcing the anastomotic site, the annular structure 3 comprises a first edge 31 and a second edge 32, and one end of the first edge 31 is hinged to one end of the second edge 32, the other end of the first edge 31 is connected with the other end of the second edge 32 in a clamped mode.

A clamping groove 311 is provided in the other end of the first edge 31, and the other end of the second edge 32 is provided with a buckle 321, the other end of the first edge 31 and the other end of the second edge 32 are connected with the buckle 321 fastening a clamping groove 311 in a matched mode.

The inner side of the large end is provided with a plurality of tooth-shaped structures 5 for preventing the intestinal canal from slipping off.

The elastic horn-shaped openings 4 is detachable.

The operation process of the embodiment is as follows:

① Pre-measuring the diameter of an intestinal canal to be matched;

② Two sides of the intestinal canal are respectively arranged at two large ends of the anastomat, and the edge of the intestinal canal is buckled on the tooth-shaped structure of the anastomotic position;

③ The two sections of intestines are respectively fastened with an annular structure for reinforcing;

④ Fourthly, the two sections of intestinal pipes are closed up to the middle, so that the intestinal tract anastomosis is directly completed, and the alignment is accurate.

The beneficial effects of the present invention are:

1, Two anastomosed intestines in the embodiment are relatively static, so the trouble that the intestinal canal needs to be adjusted when being matched with other assembling modes is avoided;

2, The operation is simple, the success rate is high, the wound is small, and the original physiological result of the digestive tract is ensured as much as possible, and the intestines are anastomosed with the end to end, while having the characteristic of reducing the incidence rate of the anastomotic leakage after intestinal anastomosis.

3, The invention can be applied for both open surgery and laparoscopic surgery.

4, The invention can be applied for a wider range of bowel, such as the small intestine, colon, sigmoid colon and rectum.

5, The invention can significantly shorten the time of intestinal anastomosis, and can reduce the difficulty of laparoscopic suture, and it is suitable for beginners.

EMBODIMENTS

With reference to FIG. 1 to FIG. 8, an absorbable and unidirectional compressive intestinal anastomosis device, comprising a first through pipe portion 1 and a second through pipe portion 2 which are matched mutually and which are made of a human acceptable degradation material; the first through pipe portion 1 can move back and forth relative to the second pipe portion 2 along a common axial direction thereof, and the first through pipe 1 and the second through pipe 2 are inseparable; The first through pipe portion 1 and the second through pipe portion 2 respectively comprise a large end (11,21) and a small end, and the large ends (11,21) are for fixing the intestinal canal, and the small end of the second through pipe portion 2 is sheathed into the small end of the first through pipe portion 1. The two large ends (11, 21) are consistent in size; when the first through pipe portion 1 moves relative to the second through pipe portion 2, the two large ends (11, 21) are drawn close to each other to achieve an intestine-intestine and end-end anastomosis.

Each of the inner side of the large end of the first through pipe portion 1 and the inner side of the large end of the second through pipe portion 2 is provided a circle of boss (14,24), and a plurality of through grooves 22 are provided on the inner side of the wall of the large end of the second through pipe portion 2 at intervals in the circumferential direction, a plurality of first racks 12 at intervals in the circumferential direction form the wall of the small end of the first through pipe part 1 in the axial direction, the first rack 12 penetrates through the through groove 22 and is movable along the through groove 22;

A plurality of second racks 23 at intervals in the circumferential direction form the wall of the small end of the second through pipe part 2, and there is a sliding groove 13 at every abutment of the first racks 12 and the second racks 23; the second rack 23 and the first rack 12 are arranged in a staggered mode, the first rack 12 and the second rack 23 are matched to form a closed space;

The tail ends of the first racks 12 and that of the second racks 23 are connected through a circular ring (15,25) respectively;

The outer side of circular ring at the ends of the small end of the first through pipe portion 1 and that of the second through pipe portion 2 are provided with gradually-expanded elastic horn-shaped openings 4 respectively; when the first through pipe portion 1 closes up or opens relative to the second through pipe portion 2, the elastic horn-shaped openings 4 of the two ends open or are squeezed into the large ends 11 of the first through pipe portion 1 or the large ends 21 of the second through pipe portion 2 respectively.

Figure 1:
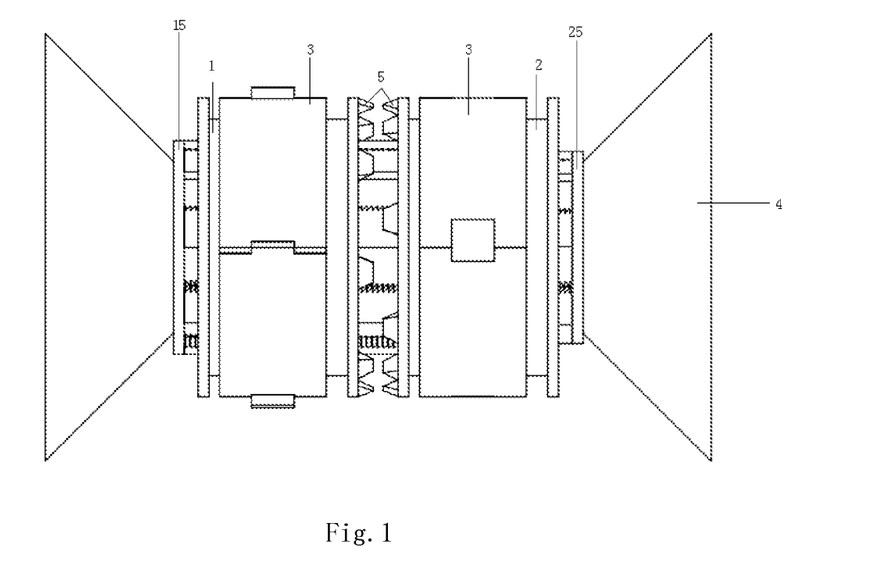
FIG. 1 is a view of an integral structure of the present invention.
Figure 2:
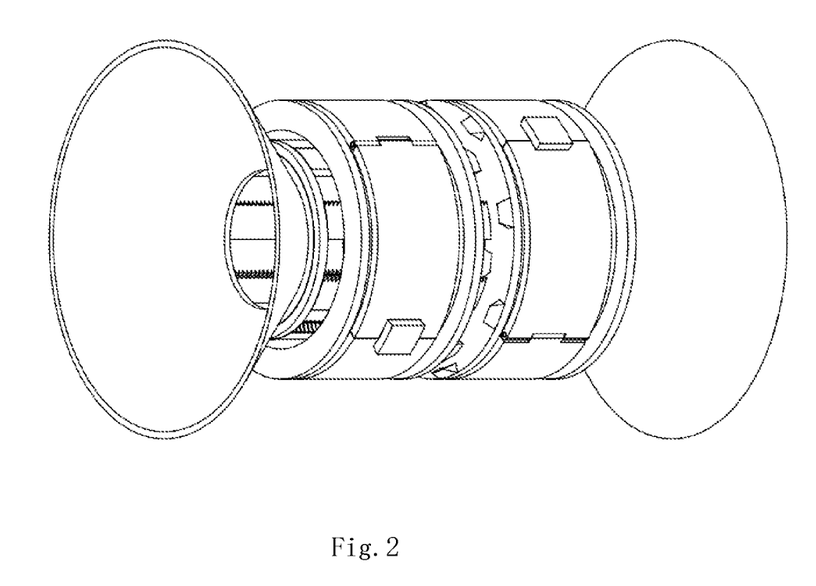
FIG. 2 and FIG. 3 are perspective views of the overall structure of the present invention.
Figure 3:
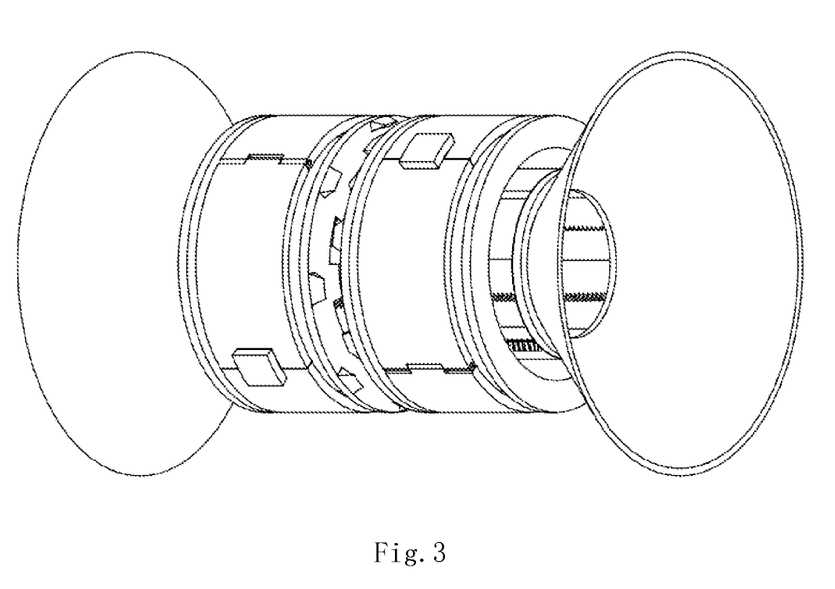
Figure 4:
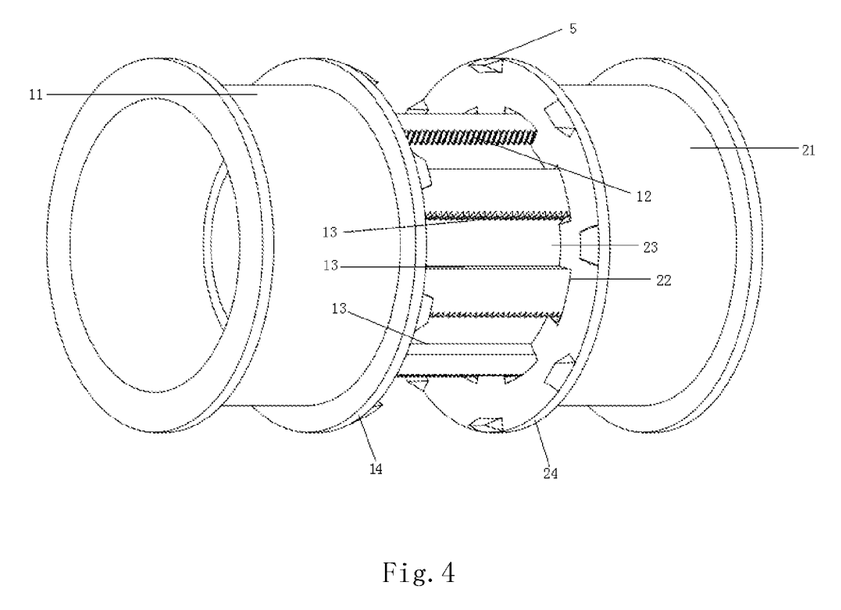
FIG. 4 is a view showing a state in which the first through pipe portion of the present invention is unfolded with respect to the second through pipe portion.
Figure 5:
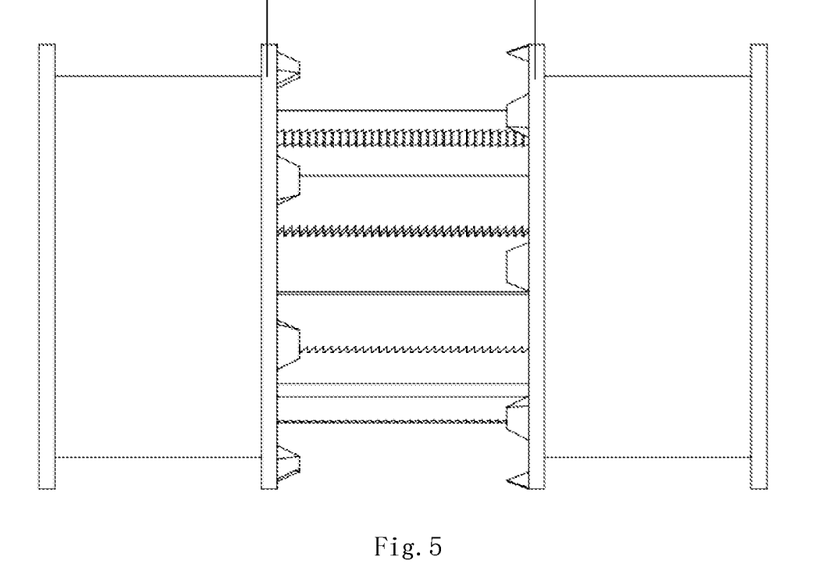
FIG. 5 is a schematic plan view showing the state in which the first through-pipe portion of FIG. 4 is unfolded with respect to the second through-tube portion.
Figure 6:
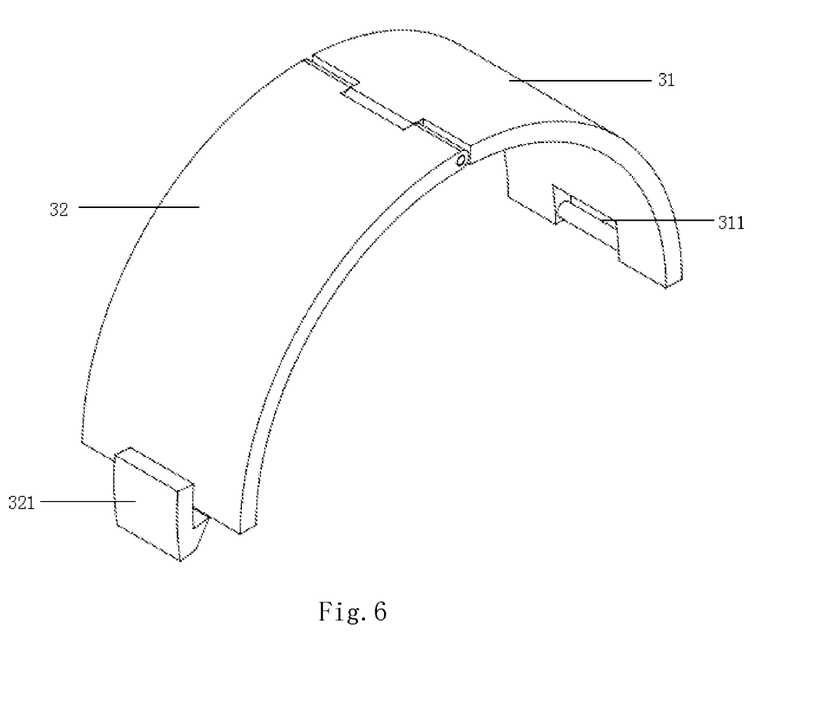
FIG. 6 and FIG. 7 are schematic perspective views of the annular structure of the present invention, respectively.
Figure 7:
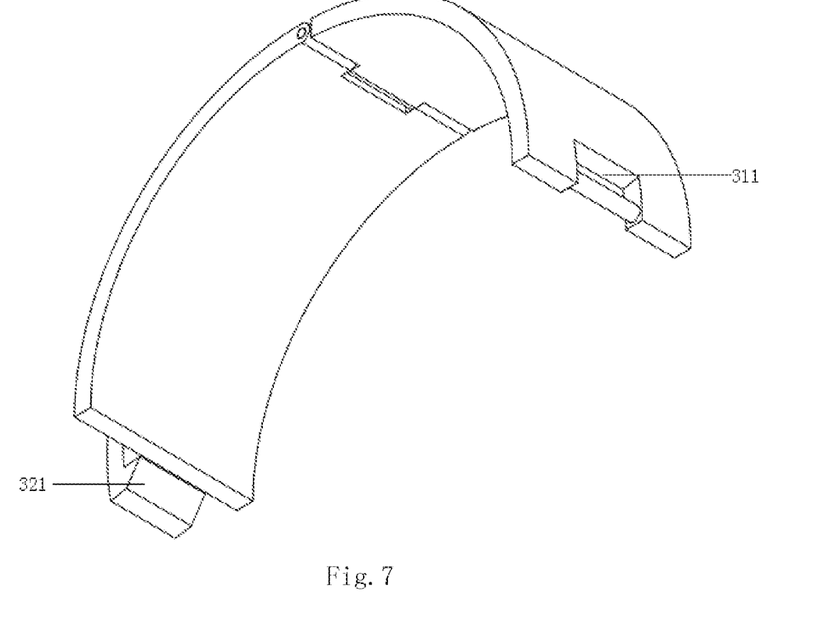
Figure 8:
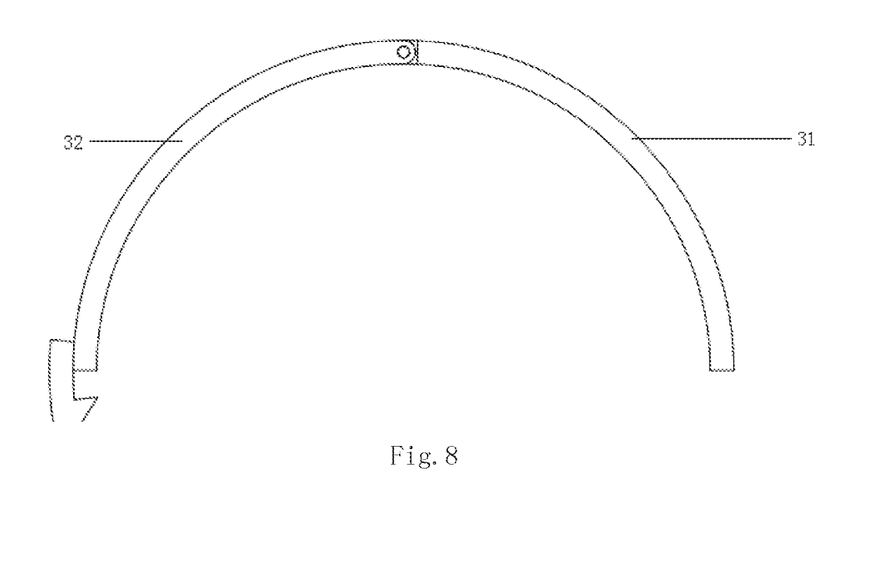
FIG. 8 is a schematic view showing the planar structure of the annular structure of the present invention.
Figure 9:
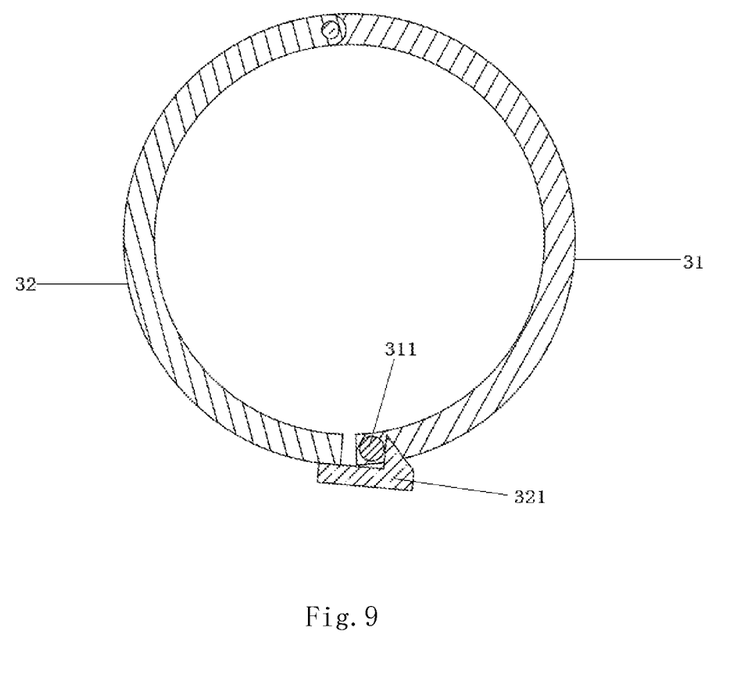
FIG. 9 is a section view of the annular structure of the present invention.

The invention further comprises an annular structure 3 which is arranged in the circumferential direction and is used for reinforcing the anastomotic site, the annular structure 3 comprises a first edge 31 and a second edge 32, and one end of the first edge 31 is hinged to one end of the second edge 32, the other end of the first edge 31 is connected with the other end of the second edge 32 in a clamped mode.

A clamping groove 311 is provided in the other end of the first edge 31, and the other end of the second edge 32 is provided with a buckle 321, the other end of the first edge 31 and the other end of the second edge 32 are connected with the buckle 321 fastening a clamping groove 311 in a matched mode.

The inner side of the large end is provided with a plurality of tooth-shaped structures 5 for preventing the intestinal canal from slipping off.

The elastic horn-shaped openings 4 is detachable.

The operation process of the embodiment is as follows:

① Pre-measuring the diameter of an intestinal canal to be matched;

② Two sides of the intestinal canal are respectively arranged at two large ends of the anastomat, and the edge of the intestinal canal is buckled on the tooth-shaped structure of the anastomotic position;

③ The two sections of intestines are respectively fastened with an annular structure for reinforcing;

④ Fourthly, the two sections of intestinal pipes are closed up to the middle, so that the intestinal tract anastomosis is directly completed, and the alignment is accurate.

Two anastomosed intestines in the embodiment are relatively static, so the trouble that the intestinal canal needs to be adjusted when being matched with other assembling modes is avoided, and the alignment is accurate. Moreover, the operation is simple, the success rate is high, the wound is small, and the original physiological result of the digestive tract is ensured as much as possible, and the intestines are anastomosed with the end to end, while having the characteristic of reducing the incidence rate of the anastomotic leakage after intestinal anastomosis.

The contents of the embodiments of the present invention are just a list of implementation forms of the inventive concept, the scope of the invention should not be considered as limited to the specific forms set forth in the embodiments, the protection scope of the invention is also applicable to equivalent technical means which can occur to those skilled in the art according to the conception of the invention.

The invention claimed is:

1. An absorbable and unidirectional compressive intestinal anastomosis device, comprising a first through pipe portion and a second through pipe portion which are matched mutually and which are made of a human acceptable degradation material; wherein, the first through pipe portion can move back and forth relative to the second through pipe portion along a common axial direction thereof, and the first through pipe portion and the second through pipe portion are inseparable; the first through pipe portion and the second through pipe portion respectively comprise a large end and a small end, and the large ends are for fixing the intestinal canal, and the small end of the second through pipe portion is inserted into the small end of the first through pipe portion; the two large ends are consistent in size; when the first through pipe portion moves relative to the second through pipe portion, the two large ends are drawn close to each other to achieve an intestine-intestine and end-end anastomosis;

each of the inner side of the large end of the first through pipe portion and the inner side of the large end of the second through pipe portion is provided a circle of boss and a plurality of through grooves at intervals in a circumferential direction of the first and the second through pipe portions;

a plurality of first racks at intervals in the circumferential direction form the wall of the small end of the first through pipe portion in the axial direction, and each of the plurality of first racks penetrates through each of the plurality of through grooves of the second through pipe portion and is movable along the plurality of through grooves of the second pipe through portion;

a plurality of second racks at intervals in the circumferential direction form the wall of the small end of the second through pipe portion;

each of the plurality of first racks and the plurality of second racks has a sliding groove at each side and a tail end;

the plurality of second racks and the plurality of first racks are arranged in a staggered mode, the plurality of first racks and the plurality of second racks are matched to form a closed space;

the tail ends of the plurality of first racks are connected through a first circular ring and the tail ends of the plurality of second racks are connected through a second circular ring;

the outer side of each of the circular rings are provided with gradually-expanded elastic horn-shaped openings respectively; when the first through pipe portion closes up or opens relative to the second through pipe portion, the elastic horn-shaped openings open or are squeezed into the large ends of the first through pipe portion or the large ends of the second through pipe portion respectively.

2. An absorbable and unidirectional compressive intestinal anastomosis device according to claim 1, wherein further comprises an annular structure which is arranged in the circumferential direction and is used for reinforcing an anastomotic site, the annular structure comprises a first arcuate component and a second arcuate component, and one end of the first arcuate component is hinged to one end of the second arcuate component, the other end of the first arcuate component is connected with the other end of the second arcuate component in a clamped mode.

3. An absorbable and unidirectional compressive intestinal anastomosis device according to claim 2, wherein a clamping groove is provided in the other end of the first arcuate component, and the other end of the second arcuate component is provided with a buckle, the other end of the first arcuate component and the other end of the second arcuate component are connected with the buckle fastening the clamping groove in a matched mode.

4. An absorbable and unidirectional compressive intestinal stapler anastomosis device according to claim 2, wherein the inner side of the large end of the first through pipe portion and the inner side of the large end of the second through pipe portion is provided with a plurality of tooth-shaped structures for preventing the intestinal canal from slipping off.

5. An absorbable and unidirectional compressive intestinal anastomosis device according to claim 4, wherein the elastic horn-shaped openings are detachable.

* * * * *